United States Patent [19]

Styers et al.

[11] Patent Number: 5,305,742
[45] Date of Patent: Apr. 26, 1994

[54] ENDOTRACHEAL TUBE HOLDER

[75] Inventors: James Styers, Gilbert, Ariz.; Claude Twogood, Littleton, Colo.

[73] Assignee: Dale Medical Products, Inc., Plainville, Mass.

[21] Appl. No.: 939,299

[22] Filed: Sep. 2, 1992

[51] Int. Cl.$^5$ .............................................. A61M 16/00
[52] U.S. Cl. ....................... 128/207.17; 128/DIG. 26; 604/178
[58] Field of Search ....................... 128/207.14, 207.17, 128/DIG. 26; 24/135 R, 135 A, 135 N, 136 B, 569, 486; 439/909, 778, 779, 807; 604/174, 178, 179

[56] References Cited

U.S. PATENT DOCUMENTS

| | | | |
|---|---|---|---|
| 2,190,824 | 2/1940 | Cook | 24/569 X |
| 2,218,210 | 10/1940 | Mebold | 24/569 X |
| 2,693,182 | 11/1954 | Phillips | 128/200.26 |
| 2,820,457 | 1/1958 | Phillips | 128/200.26 |
| 2,908,269 | 10/1959 | Cheng | 128/12 |
| 3,602,227 | 8/1971 | Andrew | 128/207.17 |
| 3,760,811 | 9/1973 | Andrew | 128/207.17 |
| 4,249,529 | 2/1981 | Nestor et al. | 128/207.17 |
| 4,449,527 | 5/1984 | Hinton | 128/207.17 |
| 4,520,813 | 6/1985 | Young | 128/207.17 |
| 4,530,354 | 7/1985 | Froilan | 128/207.17 |
| 4,683,882 | 8/1987 | Laird | 127/207.17 |
| 4,744,358 | 5/1988 | McGinnis | 128/207.17 |
| 4,774,944 | 10/1988 | Mischinski | 128/207.17 |
| 4,932,943 | 6/1990 | Nowak | 604/180 |
| 4,986,815 | 1/1991 | Schneider | 604/180 |
| 5,026,352 | 6/1991 | Anderson | 604/178 |
| 5,069,206 | 12/1991 | Crosbie | 128/207.17 |
| 5,105,807 | 4/1992 | Kahn et al. | 128/207.18 |

FOREIGN PATENT DOCUMENTS

| | | | |
|---|---|---|---|
| 338092 | 6/1921 | Fed. Rep. of Germany | 24/135 R |
| 366426 | 12/1938 | Italy | 24/243 |
| 196447 | 10/1985 | Japan | 24/135 R |
| 174179 | 6/1935 | Switzerland | 24/135 R |
| 1085864 | 10/1967 | United Kingdom | 439/807 |

OTHER PUBLICATIONS

240 Dale Tracheostomy Tube Holder (brochure).
Artec, Artec Endomask (brochure).
Hudson Endotracheal Tube Holder, 88074, Oct., 1984.
Respironics Inc., SecureEasy, 246015, Jun. 15, 1989.
Ximedix, Endo-Secure, AACN, May, 1990.

*Primary Examiner*—Edgar S. Burr
*Assistant Examiner*—Eric P. Raciti
*Attorney, Agent, or Firm*—Wolf, Greenfield & Sacks

[57] ABSTRACT

An endotracheal tube holder providing enhanced patient comfort and easy and secure attachment of various sized tubes. The holder includes a multi-component plastic clamping device having an inner bite block and straps for maintaining the device in position. The device further includes a support member with a barrel, and a cylinder movable within the barrel, and complimentary bores through the barrel and cylinder which release the tube when the bores are aligned and clamp down on the tube when the bores are in various unaligned positions.

23 Claims, 4 Drawing Sheets

ENDOTRACHEAL TUBE HOLDER

This invention relates to an endotracheal tube holder which provides enhanced patient comfort and security, and which utilizes a movable barrel and cylinder element with alignable bores for the rapid and secure engagement of various sized endotracheal tubes.

BACKGROUND OF THE INVENTION

Endotracheal (ET) tubes are used to ventilate patients for resuscitation, anesthesia and other critical care procedures. Stabilizing and securing the endotracheal tube is of vital importance. Traditionally, ET tubes have been secured by placing adhesive tape on the tube and affixing it to the face. Because the tape must be removed frequently for suctioning and possible repositioning, considerable skin breakdown can occur. This often leads to infection.

Ensuring tube security is the primary role of the ET tube holder. Tube stabilization is vital to prevent accidental or self extubation and to prevent tube movement which may cause airway trauma.

The endotracheal tube holder of this invention is intended to address and solve the above problems, and others, by: stabilizing the tube securely and easily without skin irritation and breakdown; discouraging self or accidental extubation; providing easy access to the oral cavity for oral hygiene and suctioning; preventing tube occlusion by the patient; and providing patient comfort.

Accordingly, it is an object of the present invention to provide an endotracheal tube holder having the following features and benefits:

- Effectively secures ET tube both at the tube and to the head
- Eliminates skin breakdown of face and neck
- Allows for easy access to oral cavity for suctioning and oral care
- Prevents tube occlusion by patient
- Unaffected by secretions
- Easily applied
- Easily adjusted
- Easily repositioned on tube
- Reduced incidence of tube displacement and accidental extubation
- Prevents airway trauma caused by external tube movement
- Provides convenient way to manage inflating tube
- Provides patient comfort
- Saves nursing time
- Fits a range of tube sizes (e.g., adult tube sizes 6 mm-9 mm OD, or children's tube sizes 4 mm-6 mm OD).

SUMMARY OF THE INVENTION

The endotrachael tube holder of this invention is a multi-component plastic clamping device which is positioned in front of the patient's mouth and held in position by one or two sets of straps which engage either side of the device and encircle the back of the head. In addition, an inner bite block may be provided to prevent the patient from occluding the tube and to further stabilize the device. The clamping device may be molded as four pieces to include: a face guard, barrel, cylinder and coupling. A pair of complimentary bores are provided in the barrel and cylinder through which the ET tube passes, and relative movement between the barrel and cylinder alternatively releases and secures the ET tube in position. The clamping device can be constructed of less than four pieces, as long as relative movement between the barrel and cylinder is provided.

The face guard is relatively flexible support member which inclues the inner bite block and a pair of outwardly-directed flanges for engaging the strap(s). The barrel is attached to the guard and is T-shaped—the lower leg of the "T" sits within a central aperture in the guard, while the upper cross leg of the "T" lies in front of the guard. The cylinder slides within the outer cross leg of the barrel and both the barrel and cylinder have a pair of complimentary bores through which the ET tube passes. The bores can be aligned to release the tube, or unaligned to varying degrees to frictionally engage tubes of varying outer diameter (OD) which pass between them. The coupling may engage external screw threads on one end of the cylinder for moving the cylinder relative to the barrel and thus adjusting the size of the opening formed by the complimentary bores in the cylinder and barrel. The complimentary bores securely engage a range of endotracheal tube diameters without occluding the same.

One of the goals of this ET tube holder is to eliminate skin breakdown. The holder does not generate pressure points or adhere to the skin in any way. The face guard is made of a thermoplastic rubber to comfortably fit against the face and does not contact or irritate the corners of the mouth, as will adhesive tape, twill tape and many other commercial holders. This eliminates the lip erosion that frequently occurs. Additionally, the straps are constructed of a soft hypoallergenic material. A layer of cotton contacts the skin, providing comfort to the patient, and further preventing the occurrence of irritation and skin breakdown on the face and neck. The outwardly directed flanges on the face guard hold the straps away from the patient's cheeks.

These and other features will be more particularly described by the following detailed description and drawings of certain preferred embodiments.

DETAILED DESCRIPTION

Figure 1:
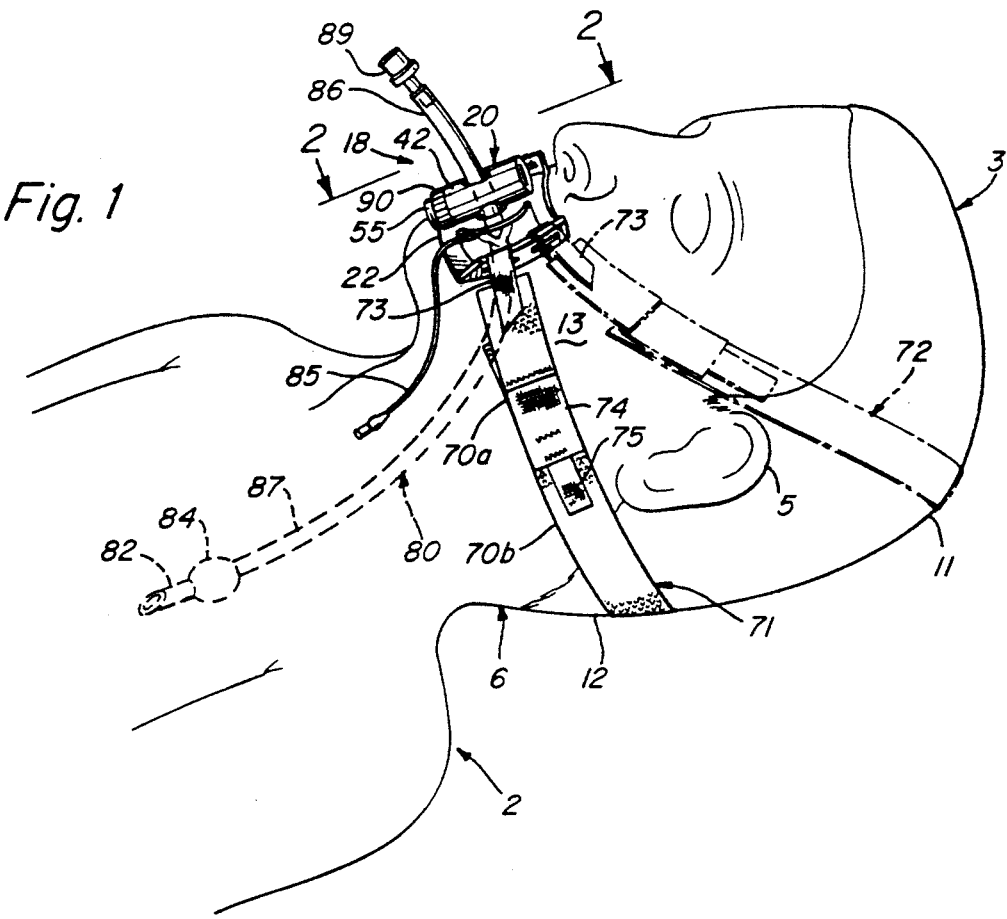
FIG. 1 is a perspective view of the endotracheal tube (ET) holder of this invention in use, as positioned on the patient's head.

Referring now to the drawings, and in particular FIG. 1, an endotracheal tube (ET) holder 18 of this invention is shown in use as positioned on a patient 2. The ET holder 18 has a plastic clamp member 20 positioned at the patient's mouth and is held in position by a lower strap 71 which extends below the ears 5 and around the back of the head near the base of the skull, i.e., at the occipital region 12 where the head 3 meets the neck 6. An upper strap 72 may also be used for added security with active or agitated patients. The upper strap encircles the head above the ears 5 and around the crown 11 of the head.

Figure 5:
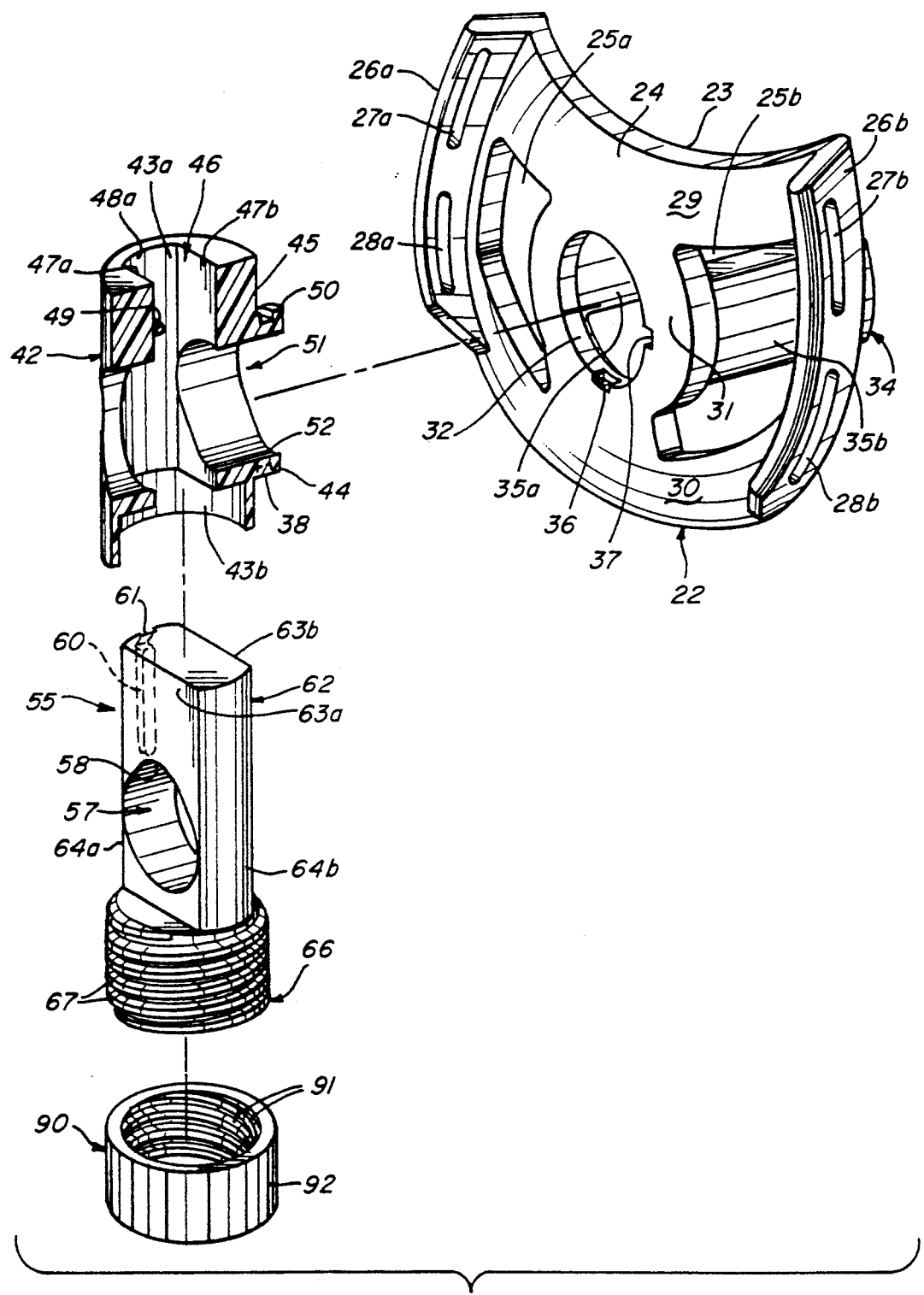
FIG. 5 is an exploded perspective view showing how the face guard, barrel, cylinder and coupling fit together, with the barrel in vertical alignment, and further including an extra locating notch for an alternative horizontal barrel configuration.

The clamp member 20 is a multi-component molded plastic device (see FIG. 5). It includes a T-shaped barrel 42 affixed to a face guard 22, and a separate cylinder 55 movable within the barrel and carrying a coupling 90 for adjustably maintaining the cylinder in a variety of positions within the barrel. By adjusting the position of the cylinder within the barrel, a variable sized opening is provided by complimentary apertures through the barrel and cylinder to frictionally engage a plurality of differently sized (i.e., different outer diameter OD) ET tubes.

As shown in FIG. 1, the ET tube 80 has a proximal portion 87 positioned within the patient's trachea with an inflatable balloon 84 adjacent the proximal end 82 for helping secure the tube within the trachea, and a distal tube portion 86 which exits the mouth and is secured at its distal end in adaptor 89 to a respirator (not shown). A branch inflation tube 85 extends from the ET tube out of the mouth with a distal coupling for a syringe or the like for inflating the balloon 84.

Figure 2:
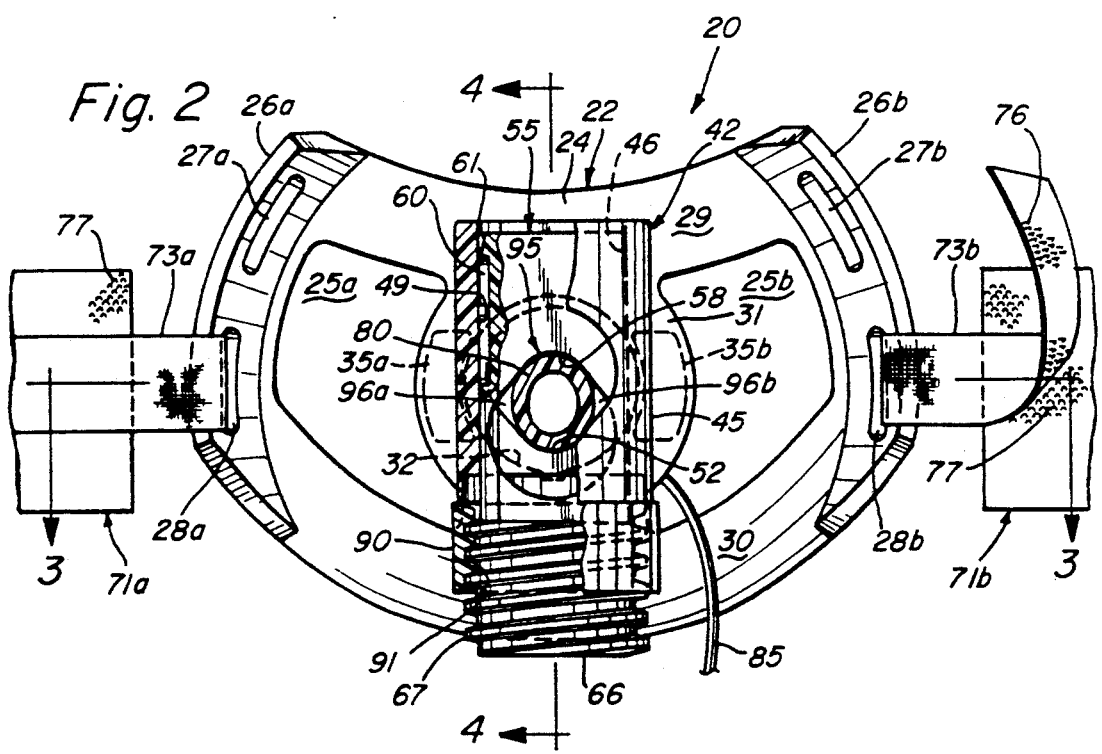
FIG. 2 is a front elevational view, partially broken away, as seen along line 2—2 of FIG. 1, showing the complimentary bores of the cylinder and barrel unaligned and frictionally engaging the ET tube.
Figure 3:
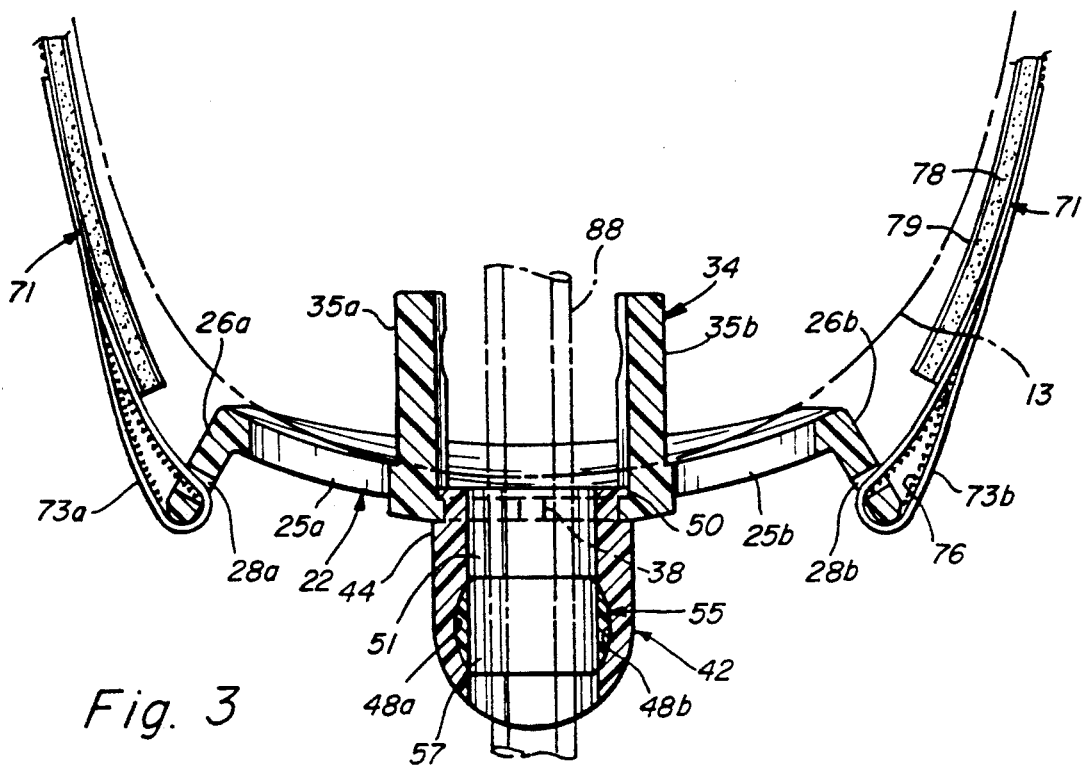
FIG. 3 is a cross-sectional view as seen along line 3—3 of FIG. 2, showing the rim of the barrel which is snap fit within an aperture on the face guard.
Figure 4:
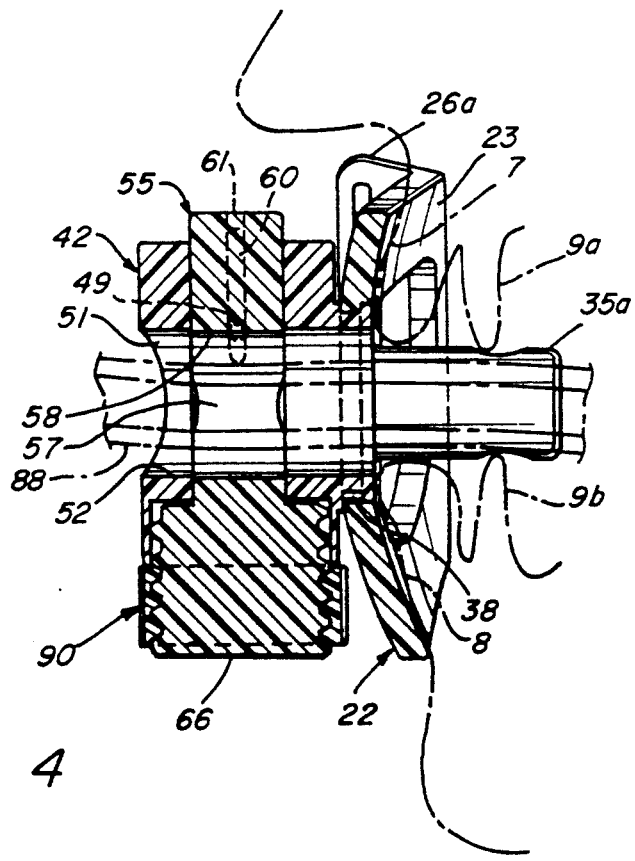
FIG. 4 is a cross-sectional view as seen along line 4—4 of FIG. 2, but with the complimentary bores of the cylinder and barrel aligned to release and permit easy passage of the ET tube therethrough.

As shown in FIGS. 2–4, an intermediate portion 88 of the ET tube passes through the clamp member 20. More specifically, intermediate tube portion 88 is substantially horizontally disposed and passes between opposing left and right side arms 35a, 35b of an inner bite block 34 and then through horizontal tube bores 51 and 57 in the barrel and cylinder respectively. Each of the bores 51 and 57 is substantially circular with a diameter substantially greater than the outer diameter of the largest ET tube used (to permit easy slidable passage). The bores further include opposing complimentary extensions which enlarge the circular bore, with tube bore 51 (in barrel 42) having a lower arcuate extension 52 and tube bore 57 (in cylinder 55) having an upper arcuate extension 58. The cylinder 55 is slidably movable within a vertical cylindrical bore 46 to enable the complimentary tube bores 51 and 57 to be moved from a first substantially aligned position (see FIG. 4) where the ET tube 80 passes freely therethrough, to a plurality of substantially unaligned positions (see e.g., FIG. 2) where the upper and lower tube extensions 58, 52 form an arcuate opening which frictionally engages the ET tube 80 around a substantial portion (i.e., 50% or greater) of the tube OD without significant occlusion of the tube. More preferably, the bores engage 70% or more of the OD of the tube. The opening 95 formed by the unaligned bores is substantially circular with opposing tapered extensions 96a, 96b at either side (see FIG. 2). The ET tube 80 is thus held securely to prevent extubation or irritating movement within the trachea. The arcuate extensions 58, 52 are particularly preferred with smaller tube OD's (e.g., 7 mm or less) because they form a more secure engagement without occluding the tube. However, other bore shapes may be used without extensions (e.g., substantially circular or oval), and non-arcuate extensions may also be suitable.

The various components of clamp 20 will now be described in greater detail (see FIGS. 2-5). Face guard 22 is a molded plastic member made of a flexible thermoplastic rubber, e.g., Pellethane polyurethane, durometer 85A, sold by Dow Chemical of Midland, Mich. Guard 22 has a smooth arcuate inner surface 23 which contacts the patient's face above the upper lip 7 and below the lower lip 8 and is curved outwardly from the face so it will not contact the delicate corners of the mouth which are prone to irritation. The bite block 34 extends into the mouth, between the patient's upper and lower teeth 9a, 9b which rest on the upper and lower surfaces respectfully of the parallel bites 35a, 35b. The external (outside of the mouth) portion of guard 22 includes a central cylindrical support member 31 (from which the bite block extends) having a central aperture 32 which receives a snap-fit rim 50 of the barrel 42. Extending above and below the central support member 31 are upper and lower arcuate arms 29, 30 respectively which are joined by opposing and outwardly extending side flanges 26a, 26b. Large oral access openings 25a, 25b are formed between the central member 31, upper and lower arms 29, 30 and flanges 26a, 26b which permit easy access to the patient's mouth for oral hygiene or suctioning. Also, the inflation tube 85 is preferably passed through one of these openings 25 for ready availability.

The flanges 26a, 26b extend away from the face 13 (see FIG. 3) and have pairs of upper and lower slots 27, 28 to receive end fastening tabs 73 from the straps 71, 72 (see FIGS. 1-2). This prevents any irritating frictional contact between the fastening members and face. The straps 71, 72 are preferably hypo-allergenic cotton-lined pile with a foam inner layer 78 and a tear-resistant looped outer layer 77 for engaging hook-type fasteners. The hook-type end fasteners 73a, 73b are looped through the slots 27a, 27b in the flanges and adjustably and releasably attached to the outer layer. A two piece strap 70a, 70b is provided with an elastic portion 74 for limited stretch and an adjustable connecting hook fastener 75 between the two strap portions.

Figure 6:
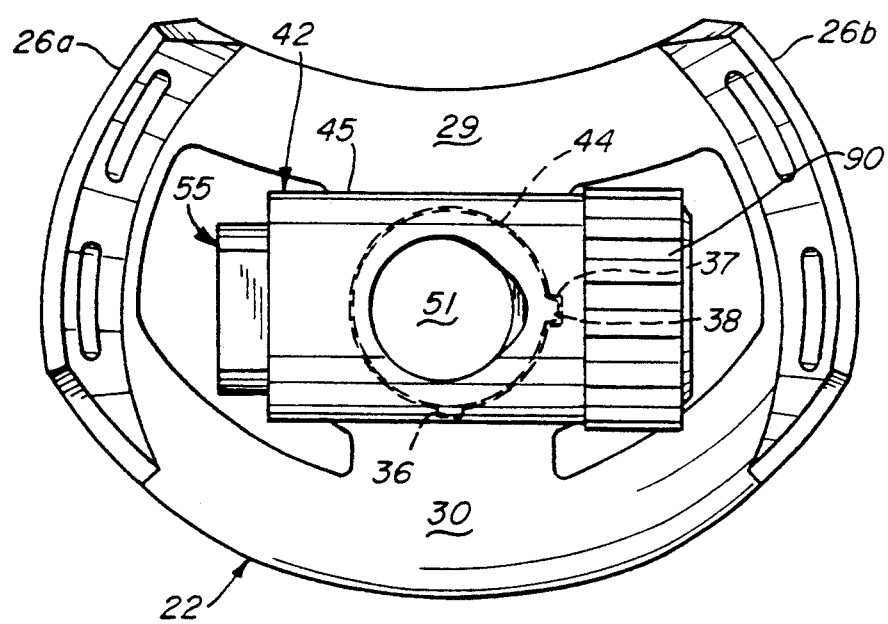
FIG. 6 is a schematic, front elevational view of the alternative horizontal barrel configuration.

As shown in FIG. 5, the T-shaped barrel 42 has a lower leg 44 which is affixed within the central aperture 32 of the guard and an upper cross leg 45 which lies vertically in front of the central guard portion 31. The lower leg 44 has a notched rim 50 which can be snap fit within the aperture 32 to prevent relative movement between the barrel and guard. In this preferred embodiment, the cross leg 45 is vertically disposed and a vertical barrel notch 36 is provided at the bottom of aperture 32 to receive locating tab 44 on the barrel and secure proper alignment of the barrel and cylinder. In an alternative embodiment (see FIGS. 5–6), a horizontal notch 37 may be provided at either side of the aperture 32 to secure horizontal alignment of the barrel and cylinder. While the barrel and cylinder can be aligned at any angle, the vertical configuration maximizes access to the oral access apertures 25a, 25b and is thus preferred. The barrel and guard can alternatively be molded as a unitary piece.

With regard to barrel 42 as shown in FIG. 5, the horizontally-disposed tube bore 51 (for ET tube 80) extends through both the lower leg 44 and cross leg 45 of the T-shaped barrel, and includes the lower extension 52. A vertically-disposed cylindrical bore 46 (for cylinder 55) extends through the cross leg 45 and includes an upper bore portion 43a. Upper bore portion 43a includes parallel and flat front and back walls 47a, 47b and arcuate opposing side walls 48a, 48b; these are sized to slidably receive complimentary shaped walls of upper cylinder portion 62, i.e., flat front and back walls 63a, 63b and opposing arcuate side walls 64a, 64b. A pin 49 and elongated groove 60 are provided on the barrel and cylinder, respectively, to prevent the cylinder from falling out of the barrel when the tube is not present. A ramp 61 entrance to the groove 61 facilitates entry of the pin into the groove. A lower portion 43b of the cylinder bore receives the enlarged threaded end 66 of the cylinder as described hereinafter.

As further shown in FIG. 5, the cylinder 55 includes an upper shaft portion 62 with a horizontally-disposed tube bore 57 (for ET tube 80) with upper extension 58. A lower cylindrical portion 66 has external screw threads 67 which engage internal threads 91 on coupling (or nut) 90. Coupling 90 is rotated to secure the alignment of tube bores 51 and 57 in the barrel and cylinder. External grooves 92 are provided on coupling 90 to enhance the grip on the coupling. A stop is provided on the coupling 90 to prevent it from being unthreaded off of the cylinder 55.

To use the device, the coupling 90 is unthreaded as far as possible. The cylinder is pushed/pulled to align the tube bores 51, 57 in the cylinder and barrel. The adaptor 89 is removed from the distal end of the ET tube and the tube passed through the aligned tube bores 51, 57 with the bite block 34 facing toward the patient. The coupling 90 is threaded in the clockwise direction until the ET tube is tightly secured in the unaligned bores 51, 57, but the device is not tightened to such an extent as to substantially occlude the tube. The adaptor is replaced on the distal end of the tube. The strap 71 (or straps 71, 72) are attached by looping the fastening tabs 73 through the slots 28 (or slots 27 and 28) in the flanges on the face guard. The tube may be easily repositioned by first loosening the coupling 90 and then retightening the same.

Although a particularly preferred embodiment of the invention has been specifically described herein, it is to be understood that variations may be made in the construction, materials, and shapes of components without departing from the spirit and scope of the invention as defined in the appended claims.

What is claimed is:

1. A holder for securing an endotracheal tube extending from a patient's mouth, the holder comprising:
    a support member and a cylinder;
    a support member being positional in front of the patient's mouth and including a first tube bore for receiving the endotracheal tube and a cylinder bore substantially perpendicular to the first tube bore for receiving the cylinder;
    the cylinder being movable within the cylinder bore and including a second tube bore movable between an aligned position wherein the axes through the centers of the first and second tube bores are colinear and the endotracheal tube passes freely through the aligned bores, and a plurality of unaligned positions wherein the axes are non-colinear but parallel for frictionally engaging endotracheal tubes of varying diameters to prevent movement thereof and without occluding the tube;
    a coupling for adjustably maintaining the first and second tube bores in the plurality of unaligned positions; and
    attachment means for maintaining the support member in front of the patient's mouth.

2. The holder of claim 1, wherein the first and second tube bores are substantially circular.

3. The holder of claim 1, wherein the first and second tube bores are substantially oval.

4. A holder for securing an endotracheal tube extending from a patient's mouth, the holder comprising:
    a support member and a cylinder;
    the support member being positionable in front of the patient's mouth and including a first tube bore for receiving the endotracheal tube and a cylinder bore substantially perpendicular to the first tube bore for receiving the cylinder;
    the cylinder being movable within the cylinder bore and including a second tube bore movable between an aligned position wherein the axes through the centers of the first and second tube bores are colinear and the endotracheal tube passes freely through the aligned bores, and a plurality of unaligned positions wherein the axes are non-colinear but parallel for frictionally engaging endotracheal tubes of varying diameters to prevent movement thereof and without occluding the tube;
    wherein the first and second tube bores are substantially circular and include opposing extensions, the opposing extensions providing increased engagement of the tube in the plurality of unaligned positions;
    a coupling for adjustably maintaining the first and second tube bores in the plurality of unaligned positions; and
    attachment means for maintaining the support member in front of the patient's mouth.

5. The holder of claim 4, wherein the opposing extensions are substantially arcuate.

6. The holder of claim 4, wherein at least 70% of the tube is engaged when the tube bores are in at least one of the unaligned positions.

7. The holder of claim 4, wherein the cylinder bore is substantially vertically positioned.

8. The holder of claim 4, wherein the cylinder bore is substantially horizontally positioned.

9. The holder of claim 4, wherein the cylinder and cylinder bore have a complimentary pin and groove for maintaining the cylinder in the cylinder bore.

10. The holder of claim 4, wherein the external support member includes at least one oral access opening to permit suctioning of the patient's mouth.

11. The holder of claim 4, wherein the cylinder and coupling have complimentary threaded portions.

12. The holder of claim 11, wherein the coupling or cylinder includes a stop so the coupling cannot be unthreaded off the cylinder.

13. The holder of claim 4, wherein the external portion of the support member has opposing side flanges extending away from the patient's face for engaging the attachment means.

14. The holder of claim 13, wherein the attachment means is at least one strap positionable around the patient's head.

15. The holder of claim 14, wherein the at least one strap includes a means for adjusting the length of the strap.

16. The holder of claim 14, wherein the flanges have slots for receiving at least one strap.

17. The holder of claim 16, wherein the flanges have a lower set of slots for receiving a first strap extending around the head below the ears and an upper set of slots for engaging a second strap extending around the head and over the ears.

18. The holder of claim 4, wherein the support member includes a bite block positionable between the patient's teeth.

19. A holder for securing an endotracheal tube extending from a patient's mouth, the holder comprising:
a support member and a cylinder;
the support member being positionable in front of the patient's mouth and including a first tube bore for receiving the endotracheal tube and a cylinder bore substantially perpendicular to the first tube bore for receiving the cylinder;
wherein the support member includes a guard member having an inner bite block and a barrel member attached to the guard member and having the cylinder bore, and wherein the first tube bore extends through both the guard and barrel members;
the cylinder being movable within the cylinder bore and including a second tube bore movable between an aligned position wherein the axes through the centers of the first and second tube bores are colinear and the endotracheal tube passes freely through the aligned bores, and a plurality of unaligned positions wherein the axes are non-colinear but parallel for frictionally engaging endotracheal tubes of varying diameters to prevent movement thereof and without occluding the tube;
a coupling for adjustably maintaining the first and second tube bores in the plurality of unaligned positions; and
attachment means for maintaining the support member in front of the patient's mouth;
wherein the first and second tube bores are substantially circular and include opposing extensions, wherein the opposing extensions provide increased engagement of the tube in the plurality of unaligned positions.

20. The holder of claim 19, wherein the barrel member is attached to the guard member with the cylinder bore in a substantially vertical position.

21. The holder of claim 19, wherein the barrel member is attached to the guard member with the cylinder bore in a substantially horizontal position.

22. The holder of claim 19, wherein the guard member is made of a flexible plastic.

23. The holder of claim 22, wherein the guard member is arcuate and extends away from the face.

* * * * *

UNITED STATES PATENT AND TRADEMARK OFFICE
CERTIFICATE OF CORRECTION

PATENT NO. : 5,305,742
DATED : April 26, 1994
INVENTOR(S) : Styers et al

It is certified that error appears in the above-indentified patent and that said Letters Patent is hereby corrected as shown below:

Col. 4, line 9 - after "portion" insert -- 24 --.

Col. 4, line 33 - after "layer" insert -- via hooks 76 --.

Col. 4, line 46 - delete "44" and substitute -- 38 --.

Col. 5, line 3 - delete "61" and substitute -- 60 --.

Signed and Sealed this

Seventh Day of February, 1995

*Attest:*

BRUCE LEHMAN

*Attesting Officer*     *Commissioner of Patents and Trademarks*